United States Patent [19]

Shigeyasu et al.

[11] 4,062,654
[45] Dec. 13, 1977

[54] APPARATUS FOR CONTINUOUS LIQUID-PHASE OXIDATION REACTION

[75] Inventors: Motoo Shigeyasu; Takehiko Kitamura, both of Matsuyama, Japan

[73] Assignee: Matsuyama Petrochemicals, Inc., Osaka, Japan

[21] Appl. No.: 506,630

[22] Filed: Sept. 16, 1974

[30] Foreign Application Priority Data

Sept. 14, 1973 Japan .................. 48-104412

[51] Int. Cl.² .............................................. B01J 8/10
[52] U.S. Cl. ...................... 23/288 A; 23/285; 23/252 R; 23/263; 134/22 R; 134/166 R; 260/75 M; 261/121 R; 261/124; 261/126; 261/87; 239/560; 239/504
[58] Field of Search ........... 23/288 A, 285, 252, 23/263, 288 R; 134/22 R, 166 R-168 R; 260/75 M; 239/560, 561, 565, 504; 261/84, 85, 87, 121, 124, 126

[56] References Cited

U.S. PATENT DOCUMENTS

| 1,447,898 | 3/1923 | Schlossstein | 23/285 UX |
|---|---|---|---|
| 3,088,974 | 5/1963 | Cier | 23/290 X |
| 3,091,518 | 5/1963 | Kizer et al. | 23/285 |
| 3,227,701 | 1/1966 | Pennington | 23/285 X |
| 3,407,179 | 10/1968 | Carr | 23/285 X |
| 3,630,777 | 12/1971 | Ishizawa et al. | 134/22 R |

*Primary Examiner*—James H. Tayman, Jr.
*Attorney, Agent, or Firm*—Sughrue, Rothwell, Mion, Zinn and Macpeak

[57] ABSTRACT

A reaction vessel for continuously producing an aromatic carboxylic acid sparingly soluble in a solvent by liquid-phase oxidizing a corresponding alkyl aromatic compound with a molecular oxygen-containing gas in the presence of a lower aliphatic carboxylic acid solvent and an oxidation catalyst. The adhesion of the aromatic carboxylic acid on the inside wall of the reaction vessel at the interface between the vapor-phase portion and the liquid-phase portion is prevented by locating in the reaction vessel a means such as a porous annular pipe for spraying onto the inside wall of the reaction vessel above the level of the reaction liquid a part of a solvent-catalyst mixture supplied continuously to the reaction vessel.

11 Claims, 8 Drawing Figures

APPARATUS FOR CONTINUOUS LIQUID-PHASE OXIDATION REACTION

BACKGROUND OF THE INVENTION

1. Field of the Invention

The present invention relates to an apparatus for the continuous production of an aromatic carboxylic acid by liquid-phase oxidizing a corresponding alkyl aromatic compound with a molecular oxygen-containing gas in the presence of a lower aliphatic carboxylic acid solvent and an oxidation catalyst. More particularly, the invention relates to an improved reaction vessel which can be used to conduct the oxidation reaction of producing an aromatic carboxylic acid sparingly soluble in a solvent in a stable manner for a long period of time without being accompanied by the adhesion of the aromatic carboxylic acid produced on the inside wall of the reaction vessel at about the interface between the vapor-phase portion and the liquid-phase portion of the reaction system.

2. Description of the Prior Art

In producing an aromatic carboxylic acid such as, for example, terephthalic acid by the liquid-phase oxidation of the corresponding alkyl aromatic compound such as p-xylene, a continuous system wherein the liquid-phase oxidation is carried out continuously while continuously supplying a raw material alkyl aromatic compound, a solvent, an oxidation catalyst, and a molecular oxygen-containing gas into the reaction vessel and, on the other hand, continuously withdrawing the reaction product aromatic carboxylic acid from the bottom of the reaction vessel is more advantageous than a batch system because in the continuous system a product having uniform quality can be obtained in a stable manner over a long period of time.

However, in producing an aromatic carboxylic acid such as terephthalic acid using a lower aliphatic carboxylic acid such as acetic acid as the solvent, the aromatic carboxylic acid gradually crystallizes out if the reaction vessel is used for a long period since the aromatic carboxylic acid which is the reaction product is sparingly soluble in the solvent and the crystals accumulate and adhere to the inside wall, etc., of the reaction vessel. In particular, it has been confirmed that in a reaction vessel equipped with a stirrer used in a conventional reaction, a large amount of crystals adhere to the inside wall of the reaction vessel near the interface between the vapor-phase portion and the liquid-phase portion due to the influence of the stirring. If the crystals of the reaction product adhere to the inside wall of the reaction vessel as mentioned above, the effect of the stirring is decreased and the volume for the liquid portion in the reaction vessel is reduced. This makes it difficult to continue the operation in a stable manner for a long period of time. Also, since in such a case the heat of reaction accumulates in the liquid portion due to the reduction in the area of the reaction liquid surface for evaporation, the occurence of side reactions increases to reduce inevitably the yield for and the quality of the reaction product.

Therefore, in such a conventional operation for the production of an aromatic carboxylic acid, the operation inevitably must be stopped when the adhesion and accumulation of the reaction product on the inside wall of the reaction vessel becomes great, the inside of the reaction vessel must be sufficiently washed with an aqueous solution of an alkali such as sodium hydroxide to remove the accumulated material, and thereafter the operation is resumed. However, thus interruption as described above, as a matter of course, reduces the operation efficiency, results in an uneven reaction product quality throughout the long run, and increases the cost of materials and labor required for the operation.

Also, as disclosed in Japanese patent publication No. 5140/'71, an improved apparatus for producing terephthalic acid is proposed in which a small cylinder closed at the bottom is placed concentrically in a cylindrical reaction vessel to provide inside the reaction chamber a means of preventing the adhesion of terephthalic acid on the inside wall of the apparatus and a raw material mixture heated to a temperature substantially the same as the reaction temperature is supplied to the annular space between the wall of the outer cylindrical reaction vessel and the wall of the inside reaction chamber to allow the mixture to flow over the wall edge of the inside reaction chamber as an overflow or droplets of it. However, in such a proposed apparatus a double-walled complicated apparatus having a quite different structure from that of a conventional apparatus must be used and also it is necessary to pre-heat the raw material mixture to a temperature substantially the same as the reaction temperature. That is, the employment of such an apparatus is operationally and economically disadvantageous.

Thus, a satisfactory reaction vessel which can be used economically and easily for producing an aromatic carboxylic acid efficiently without being accompanied by adhesion of crystals of the aromatic carboxylic acid on the inside wall of the reaction vessel has not yet been developed.

SUMMARY OF THE INVENTION

As the result of various investigations on reaction vessels for producing an aromatic carboxylic acid the liquid-phase oxidation of the corresponding alkyl aromatic compound, it has been discovered since the catalyst is usually supplied to the reaction system as a solution in a solvent in the continuous liquid-phase oxidation because the catalyst component used in the reaction is usually a solid material containing a heavy metal such as cobalt, manganese, etc., that if a part of the catalyst-solvent mixture is sprayed onto the wall of the reaction vessel through a spraying means such as a porous annular pipe located along the inside wall of the vessel above the level of the liquid-phase portion in the reaction vessel, the adhesion of the reaction on the inside wall of the reaction vessel can be quite effectively prevented.

An object of this invention is, therefore, to provide a reaction vessel for the continuous production of an aromatic carboxylic acid, in which the adhesion of the produced aromatic carboxylic acid on the inside wall of the reaction vessel can be prevented by locating a means for spraying a part of the solvent-catalyst liquid mixture onto the inside wall of the vessel above the vapor-liquid interface of the reaction system in the reaction vessel.

Another object of this invention is to provide a reaction vessel for producing with high yield a very pure aromatic carboxylic acid by a continuous liquid-phase oxidation of the corresponding alkyl aromatic compound.

These and other objects of this invention will become apparent from the following description in connection with the accompanying drawings.

DETAILED DESCRIPTION OF THE INVENTION

According to the present invention, a reaction vessel for the continuous liquid-phase oxidation reaction for producing an aromatic carboxylic acid which is sparingly soluble in the solvent by liquid-phase oxidizing an alkyl aromatic compound with a molecular oxygen-containing gas in the presence of a lower aliphatic carboxylic acid solvent and an oxidation catalyst, is provided in which a means is located in the reaction vessel above the interface between the vapor-phase portion and the liquid-phase portion in the vessel for spraying onto the inside wall of the reaction vessel above the level of the reaction liquid a part of a solvent-catalyst liquidous mixture which is supplied continuously into the reaction system.

The apparatus of this invention will be described in greater detail by the accompanying drawings.

Figure 1:
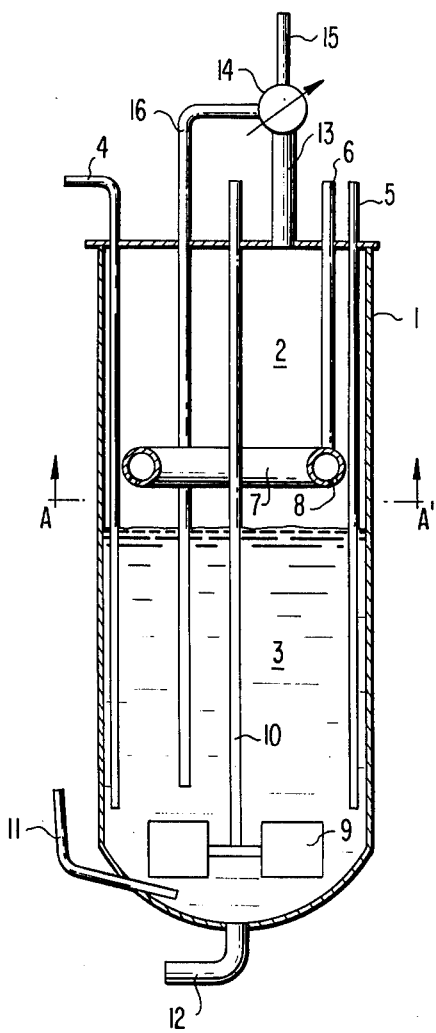
FIGS. 1, 3, 5 and 7 are schematic cross sectional views showing embodiments of the reaction vessel of this invention, respectively.
Figure 2:
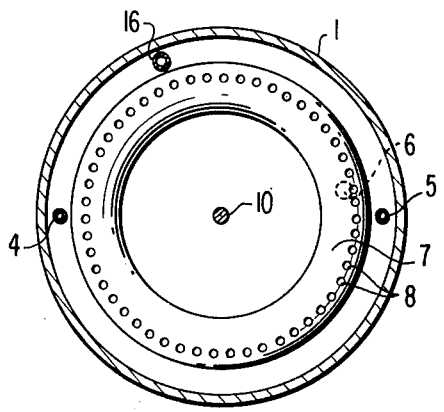
FIGS. 2, 4, 6 and 8 are schematic sectional views taken along the line A—A' of FIGS. 1, 3, 5 and 7, respectively.

In FIG. 1 which is a schematic cross sectional view showing an embodiment of the reaction vessel of this invention, a reaction vessel 1 contains a vapor-phase portion 2 and a liquid-phase portion 3. The reaction vessel is equipped with an inlet conduit 4 for supplying a raw material-solvent liquid mixture to the reaction system (only one conduit is shown in the figure but a plurality of conduits can be used for this purpose), a conduit 5 for supplying a solvent-catalyst liquidous mixture to the reaction system, and a conduit 6 for supplying a part of the solvent-catalyst liquid mixture to an annular pipe 7 located in the reaction vessel along the inside wall thereof. The annular pipe 7 has a number of small holes 8 (as shown in FIG. 2) for spraying the solvent-catalyst mixture supplied through the conduit 6 onto the inside wall of the reaction vessel above the liquid level. The reaction vessel is also equipped with a stirrer composed of a shaft 10 and a blade 9 (the stirrer shown in the figure has one set of blades but usually a plurality of sets of blades is used), a conduit 11 for introducing a molecular oxygen-containing gas, an outlet conduit 12 for the reaction product, a conduit 13 for withdrawing vapors, a condensor 14, a conduit 15 for discharging a discharge gas, and a conduit 16 for recycling the condensed liquid.

FIG. 2 is a schematic sectional top view taken along the line A—A' of the reaction vessel 1 shown in FIG. 1. In FIGS. 1 and 2, the pipe 7 can have an outer diameter of from about ⅛ to about 10 inches, preferably ½ to 5 inches, and the small holes 8 have a diameter of from about 0.3 to about 50 mm, preferably 0.5 to 20 mm. The proportion of the total surface area of the small holes 8 to the total surface areas of the pipes 7 can range from about 0.01 to about 10%, preferably 0.05 to 3%.

Figure 3:
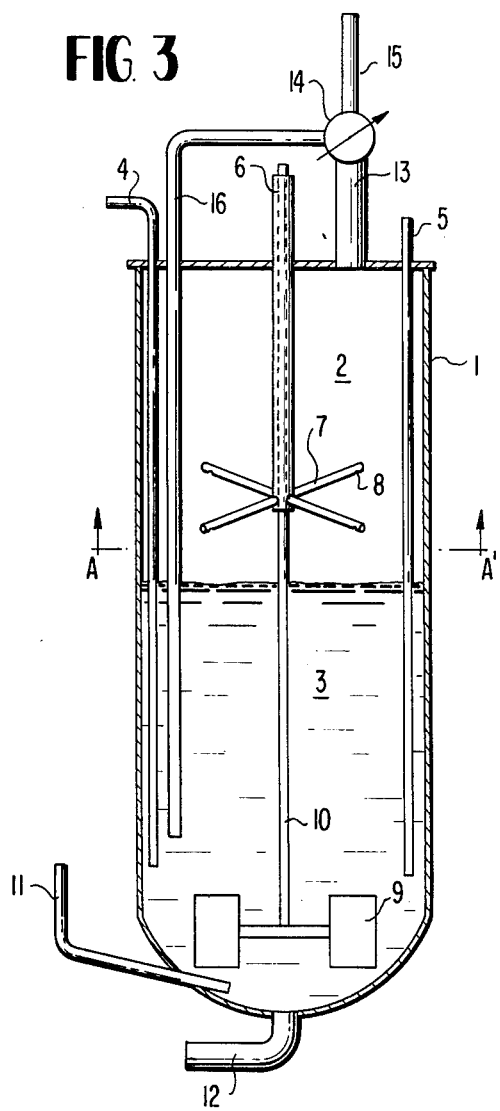
Figure 4:
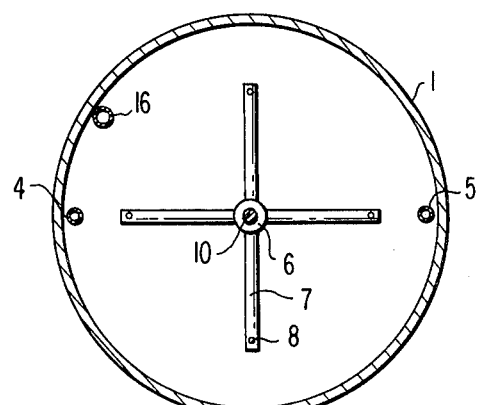

FIG. 3 shows another embodiment of the reaction vessel in which the inlet conduit for spraying the solvent-catalyst liquid mixture onto the inside wall of the reaction vessel is a hollow tube 6 surrounding a shaft 10 of the stirrer. The lower end of the hollow tube 6 is provided with a plurality of hollow pipes 7 extending at approximately right angles relative to the hollow tube 6 having small holes 8 at the end of each of the pipes 7 so that the solvent-catalyst liquid mixture can be sprayed toward the inside wall of the reaction vessel while rotating the pipes 7 in conjunction with the shaft 10. FIG. 4 is a schematic sectional view taken along the line A—A' of the reaction vessel shown in FIG. 3. In FIGS. 3 and 4, four pipes 7 are shown, but the number of the pipes can be 2 or more, preferably 3 to 8. The outer diameter of the pipes 7 and the diameter of small holes 8 can be the same as those of the reaction vessel shown in FIGS. 1 and 2. The proportion of the total surface area of the small holes 8 to the total surface area of the pipes 7 can be about 0.001 to about 0.3%, preferably 0.005 to 0.1%.

Figure 5:
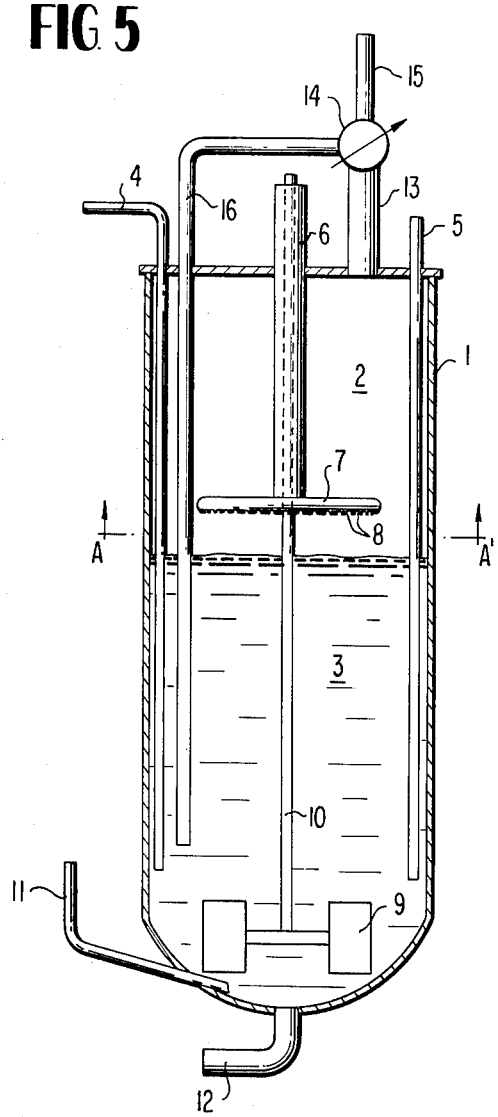
Figure 6:
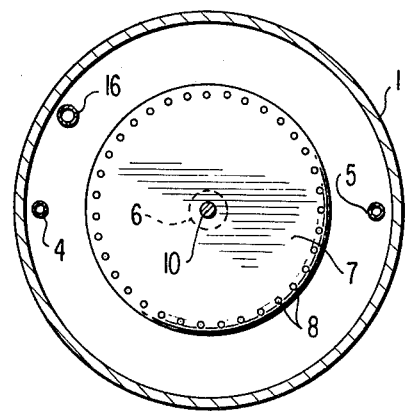

FIG. 5 shows a further embodiment of the reaction vessel of this invention in which the inlet conduit for spraying the solvent-catalyst liquid mixture is a hollow tube 6 surrounding a shaft 10 of the stirrer in the same manner as shown in FIGS. 3 and 4. The lower end of the hollow tube 6 is provided with a hollow disc 7 having small holes 8 near the portion facing the inside wall of the reaction vessel so that the solvent-catalyst liquid mixture can be sprayed toward the inside wall of the reaction vessel while rotating the disc 7 in conjunction with the shaft 10. FIG. 6 is a schematic sectional top view taken along the line A—A' of the reaction vessel shown in FIG. 5. The thickness of the hollow disc 7 can be from about ⅛ to about 10 inches, preferably ½ to 5 inches. The diameter of the small holes 8 and the proportion of the total surface area of the small holes 8 to the total surface area of the disc 7 can be the same proportions as those described for the reaction vessel shown in FIGS. 3 and 4.

Figure 7:
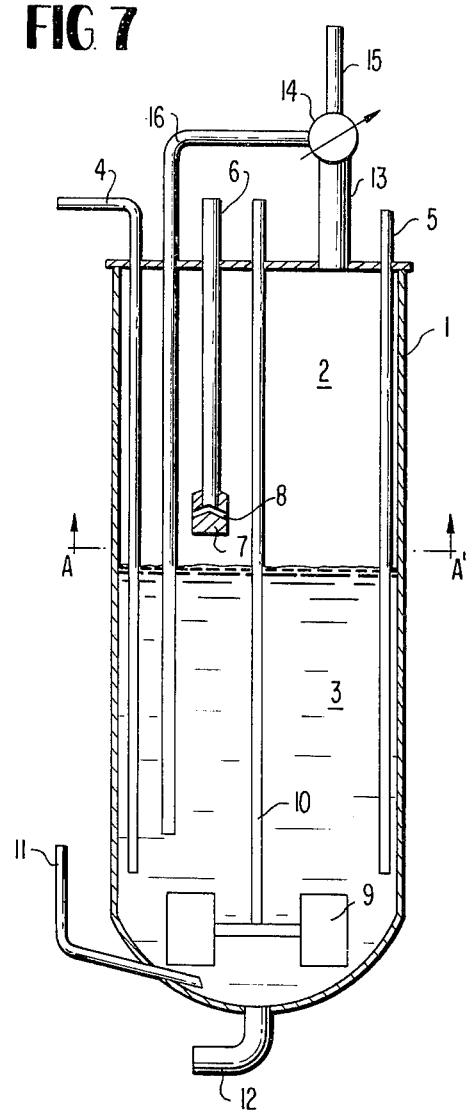
Figure 8:
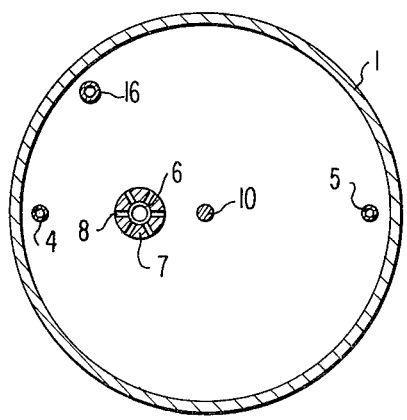

FIG. 7 shows a still further embodiment of the reaction vessel of this invention in which the inlet conduit 6 is provided, at the end thereof, with a spray nozzle 7 so that the solvent-catalyst liquid mixture can be sprayed toward the inside wall of the reaction vessel through the holes 8 of the spray nozzle. The inlet conduit 6 can be integrated with the shaft 10 as shown in FIGS. 3 and 5. FIG. 8 is a schematic sectional top view taken along the line A—A' of the reaction vessel shown in FIG. 7. The nozzle 7 which can be used in this embodiment is one having a diameter of from about ⅛ to 5 inches and a diameter for the small holes 8 ranging from about 0.2 to 20 mm.

The proportion of the opening area of the small holes to the total surface area of the nozzle 7 can range from about 0.1 to about 30%, preferably from 0.5 to 10%.

Each of the means for spraying the solvent-catalyst liquid mixture shown in FIGS. 1 to 8 can be located at a position of about 1/20 to about ⅓ times, preferably 1/15 to 1/5 times the height, i.e., the tangential length of the reaction vessel, above the liquid level (shown as a wavy line in the figures). The minimum distance between the small holes 8 of the means 7 and the inside wall of the reaction vessel can vary with the pressure of the solvent-catalyst liquid mixture supplied, rotating rate of the stirrer, etc. but generally is from about 0.01 to about 5 m, preferably 0.05 to 1 m.

The means for spraying can be provided at the end of an inlet conduit for the solvent-catalyst liquid mixture separately from the shaft of the stirrer as shown in FIGS. 1 and 2 or 7 and 8. Alternatively, the inlet conduit for the solvent-catalyst liquid mixture can be a hollow tube surrounding the shaft of the stirrer, and the means for the spraying can be provided at the end of the hollow tube and rotated together with the shaft of the stirrer, as shown in FIGS. 3 and 4 or 5 and 6. When the means for the spraying is provided independently of the stirrer as shown in FIGS. 1 and 2 or 7 and 8, the charging pressure is advantageously increased so as to force the solvent-catalyst liquid mixture toward the inside wall of the reaction vessel. On the other hand, when the means for spraying is provided around the shaft of the stirrer as shown in FIGS. 3 and 4 or 5 and 6, the solvent-catalyst liquid mixture can be sprayed toward the inside wall of the reaction vessel through the small holes using centrifugal force by rotating the spraying means with the shaft of the stirrer.

According to the reaction vessel of this invention illustrated in the accompanying drawings, the solvent-catalyst mixture continuously supplied into the conduit 6 is heated by heat exchange with the vapor in the vapor-phase portion in the reaction vessel and then sprayed through the holes 8 of, for example, an annular pipe 7 onto the inside wall of the reaction vessel at the interface area between the vapor-phase portion and the liquid-phase portion on which the crystals of the reaction product tend to adhere and accumulate. Therefore, as the result, the adhesion of the crystals of the reaction product on the inside wall of the reaction vessel is effectively prevented and thus the aromatic carboxylic acid can be continuously produced in an continuously stable manner for a long period of time.

Also, in the reaction vessel of this invention, a part of the solvent-catalyst mixture is supplied to the reaction system through the spraying means such as a porous annular pipe as described above and the remainder of the solvent-catalyst mixture is supplied through a conduit 5 of which the outlet end is disposed in the liquid-phase portion near the bottom of the reaction vessel. Thus, in the reaction vessel of this invention, the solvent-catalyst mixture is supplied from the upper portion and the lower portion of the reaction vessel separately and hence the catalyst can be quickly distributed uniformly throughout the liquid phase by the action of the stirrer to increase the yield and the quality of the aromatic carboxylic acid produced.

If the proportion of the solvent-catalyst mixture sprayed through the porous annular pipe to the total amount of the solvent-catalyst mixture to be supplied to the reaction system is too small, the effect of washing the inside wall of the reaction vessel is reduced, while if the proportion is too large, the proportion of the solvent-catalyst mixture to be supplied to the reaction system from the lower portion of the reaction vessel is reduced, which results in making it difficult to provide quickly catalyst homogeniety throughout the reaction liquid. Therefore, the proper ratio of the amount of the solvent-catalyst mixture supplied from the lower portion of the reaction vessel to the amount of the mixture sprayed through the porous annular pipe is about 2/1 to about ⅓, and the proper flow rate of the solvent-catalyst mixture supplied through the spraying means is about 0.5 to 10 times, preferably 1 to 5 times, the charge rate of the alkyl aromatic compound. The concentration of the catalyst in the solvent-catalyst mixture sprayed through the annular pipe can be about ⅓ to 10 times, preferably 1 to 5 times, that of the reaction mixture in the reaction vessel.

The reaction vessel of the invention can be used for any reactions of producing aromatic carboxylic acids sparingly soluble in lower aliphatic carboxylic acid solvents by the liquid-phase oxidation of alkyl aromatic compounds using lower aliphatic carboxylic acids as the solvent. For example, the apparatus of this invention can be used for producing terephthalic acid from p-xylene or p-diisopropylbenzene, isophthalic acid from m-xylene, trimellitic acid from psedudocumene, and naphthalene-1,8-dicarboxylic acid from acenaphthene.

The solvent used in the liquid-phase oxidation practiced using the reaction vessel of this invention is a lower aliphatic carboxylic acid having 2 to 8 carbon atoms such as, for example, acetic acid, propionic acid, butyric acid, and the like.

It is economically most advantageous to use air as the molecular oxygen-containing gas used in the liquid-phase oxidation as the oxidizing agent but a mixed gas of an inert gas prepared by burning hydrocarbons and air or oxygen, a mixed gas of nitrogen and air or oxygen, and an exhaust gas from an oxidation reaction vessel of which the concentration of oxygen has been adjusted to an appropriate value with air or oxygen can be also used as the oxidizing agent.

As the oxidation catalyst, a compound containing a heavy metal component such as cobalt, manganese, etc., is generally used but a reaction accelerator such as a bromine compound and an aldehyde can be used as the case may be.

Some of the advantages of the reaction vessel of this invention in comparison with conventional reaction vessels are as follows:

1. Since as described above the adhesion of the crystals of the reaction product on the inside wall of the reaction vessel near the interface between the vapor-phase portion and the liquid-phase portion can be prevented by spraying as fine streams a part of the solvent-catalyst liquid mixture onto the inside wall of the reaction vessel above the interface, a stable oxidation reaction can be practiced continuously for a long period of time without the need for stopping the operation of the reaction and removing the material adhering on the inside wall of the vessel with an aqueous alkali solution as in the case of employing a conventional reaction vessel, and thus a very pure product having a uniform quality can be produced with a good yield in the apparatus of the invention.

2. Since the solvent-catalyst liquid mixture is supplied to the reaction system from the lower part of the reaction liquid and from the top of the reaction liquid different from a conventional system in which the solvent-catalyst mixture is supplied from only the lower part of the reaction liquid, a uniform distribution of the catalyst in the reaction liquid is greatly accelerated to improve the quality and the yield of the reaction product.

3. Since a part of the solvent-catalyst liquid mixture is sprayed from a position above the level of the reaction liquid, the unreacted raw material which escapes as vapor from the surface of the reaction liquid into the vapor-phase portion is washed back into the reaction liquid by the solvent-catalyst liquid mixture thus sprayed from above and thus the amount of unreacted raw material lost in the vapor-phase portion is reduced to increase the efficiency of the reaction. Also, since the allowable oxygen concentration from an explosion limit standpoint increases due to the reduction in the concentration of the raw material in a vapor state in the vapor-phase portion, the oxidation reaction can be practiced safely and efficiently under a higher oxygen concentration than in a conventional method.

4. In the oxidation reaction to which the reaction vessel of this invention is applied, a large amount of bubbles form near the surface of reaction liquid in a reaction vessel when a conventional reaction vessel is employed to hinder the radiation of reaction heat and to reduce the effective area of the reaction vessel. On the other hand, when the reaction vessel of this invention is employed for such an oxidation reaction, the formation of the bubbles can also be effectively suppressed since the solvent-catalyst liquid mixture is continuously sprayed near the surface of liquid.

As described above, the reaction vessel of this invention provides the above described various excellent advantages as compared with conventional reaction vessels by providing a simple means of spraying to the inside wall of a reaction vessel a part of the solvent-catalyst liquid mixture to a conventional reaction vessel and thus the reaction vessel of this invention is industrially and economically quite advantageous.

The apparatus of this invention is, in particular, preferably applied to the reaction of producing high quality terephthalic acid suitable for use as a raw material for a direct polymerization reaction using p-xylene as the raw material.

The advantages of this invention will be explained in the following example and comparison example by reference to production of high-quality terephthalic acid from p-xylene but the scope of this invention is not to be construed as being limited to this example only.

EXAMPLE

A reaction vessel 1 having an inside diameter of 240 mm. and a height of 850 mm., and equipped with conduit 4 for supplying a raw material-solvent mixture, conduit 5 for supplying a solvent-catalyst mixture, conduit 6 for supplying a part of the solvent-catalyst mixture to the porous annular pipe 7, the porous annular pipe 7 being connected to conduit 6 for spraying the solvent-catalyst mixture onto the inside wall of the reaction vessel, stirrer 9, conduit 11 for introducing air, conduit 12 for withdrawing the reaction product, etc., as shown in FIG. 1 was used.

In the aforesaid reaction vessel were charged 12 kg. of acetic acid as a solvent and 61 g. of cobalt acetate, 3 g. of manganese acetate, and 36 g. of sodium bromide as a catalyst component and after increasing the pressure and temperature of the system to 20 kg./cm.$^2$ and 190° C. respectively, air was continuously introduced into the system through conduit 11 at a rate of 4.2 NM$^3$/kg.-p-xylene and also p-xylene was continuously supplied to the system through conduit 4 at a rate of 2.4 kg./hr. for 30 minutes. Then, while continuing the supply of air and p-xylene, a mixture of acetic acid and the catalyst component as charged in the reaction vessel but having a catalyst concentration twice as large as that of the mixture charged in the reaction vessel was supplied to the reaction system from the lower part of the reaction liquid through conduit 5 at a rate of 1.8 kg./hr. and also the acetic acid-catalyst mixture was supplied through conduit 6 at a rate of 1.8 kg./hr. and sprayed onto the inside wall of the reaction vessel from holes 8 of the annular pipe. Furthermore, acetic acid was supplied through conduit 4 at a rate of 3.6 kg./hr. together with p-xylene and on the other hand, the reaction product was intermittently withdrawn with intervals of about 10 minutes in an amount of about 2 kg. each time through conduit 12. Thus, the operation was continued for 500 hours. The property of the terephthalic acid sampled during the reaction is shown in Table 1 and the yield for the reaction product was 97 mole%. In addition, after the reaction was over, hardly any adhesion of crystals of terephthalic acid on the inside wall of the reaction vessel near the level of the reaction liquid was observed.

COMPARISON EXAMPLE

The same procedure as in the Example described above was repeated using the same reaction vessel as in the above Example except that all of the acetic acid-catalyst mixture was supplied through conduit 5 without using conduit 6 and porous annular pipe 7 connected thereto, that is, without spraying the mixture through the porous annular pipe. The property of the terephthalic acid sampled during the reaction is also shown in Table 1. As shown by the results in the table, the property of terephthalic acid became gradually inferior as the progress of the reaction and the reaction was obliged to be stopped after 50 hours. The yield for the product was 92 mole%. After the reaction was over, it was observed that crystals of terephthalic acid stuck on the inside wall of the reaction vessel near the level of the reaction liquid in a thickness of about 30 mm.

Table 1

| Reaction time (hr) | Purity (wt%) | Content of 4-Carboxybenz-aldehyde (ppm) | Molecular Extinction Coefficient* (380 mµ) | Color Difference b-Value** |
|---|---|---|---|---|
| Invention Example | | | | |
| 10 | 99.97 | 280 | 0.04 | 2.0 |
| 20 | " | " | " | 2.1 |
| 50 | " | " | " | 2.2 |
| 100 | 99.96 | 290 | 0.05 | 2.3 |
| 300 | " | 300 | " | " |
| 500 | 11 " | 310 | " | 2.5 |
| Comparison Example | | | | |
| 10 | 99.96 | 350 | 0.05 | 2.4 |
| 20 | 99.94 | 440 | 0.06 | 2.7 |
| 50 | 99.54 | 760 | 0.25 | 10.7 |

*: The absorption of a solution of 5 g. of terephthalic acid in 100 ml. of 2 N aqueous ammonia was measured spectrophotometrically at 380 mµ. and the smaller the value, the better the hue.

**: The so-called appearance obtained by measuring the reflected light of solid terephthalic acid using color-difference meter CM-20 Type made by Color Machine K. K., the b-value showing yellow (+) to blue (−), and the smaller the value the better the hue.

While the invention has been described in detail and with reference to specific embodiments thereof, it will be apparent to one skilled in the art that various changes and modifications can be made therein without departing from the spirit and scope thereof.

What is claimed is:

1. In a reaction vessel for continuous liquid-phase oxidation for producing an aromatic carboxylic acid sparingly soluble in a lower aliphatic carboxylic acid solvent by a liquid-phase oxidation of the corresponding alkyl aromatic compound with a molecular oxygen-containing gas under high temperature and high pressure in the presence of the lower aliphatic carboxylic acid solvent and an oxidation catalyst, said reaction vessel having a lower portion for holding a liquid phase and an upper portion for holding a vapor phase, said reaction vessel including a vapor outlet at the top of the reaction vessel, an outlet for the reaction product and an inlet for an oxygen-contining gas adjacent the bottom of said reaction vessel, stirring means disposed in the reaction vessel, a conduit for supplying a liquid mixture of raw material and solvent having the discharge end thereof in the lower portion of the vessel, a conduit for supplying a solvent-catalyst liquid mixture to the lower portion of the vessel adjacent the bottom of the reaction vessel, a condenser connected to said vapor outlet and a conduit disposed in communication with said condenser at one end with the discharge end disposed in the lower portion of said vessel for recycling condensed liquid, the improvement comprising a spraying means disposed in the upper portion of the vessel for supplying additional solvent-catalyst liquid mixture, having downwardly and outwardly slanted discharge holes and located at a position of about 1/20 to about ⅓ times the height of the reaction vessel above the line between the upper and lower portions of the vessel to thereby supply continuously said solvent-catalyst liquid mixture in a finely divided form onto the inside wall of the reaction vessel immediately above said line to remove reaction products deposited on said wall.

2. The reaction vessel as claimed in claim 1, wherein said means for spraying a part of the solvent-catalyst liquid mixture comprises a plurality of hollow pipes extending from the inlet conduit for said solvent-catalyst liquid mixture to be sprayed and substantially parallel to the interface between the liquid-phase portion and the vapor phase portion, said solvent-catalyst liquid mixture being sprayed through small holes at the end of each of said hollow pipes.

3. The reaction vessel as claimed in claim 2, wherein the number of said hollow pipes is 3 to 8.

4. The reaction vessel as claimed in claim 1, wherein said means for spraying a part of the solvent-catalyst liquid mixture is a hollow disc having small holes along the disc circumference near the portion facing the inside wall of the reaction vessel.

5. The reaction vessel as claimed in claim 1, wherein said means for spraying is a spray nozzle.

6. The reaction vessel as claimed in claim 1, wherein said means for spraying a part of the solvent-catalyst liquid mixture comprises a porous annular pipe provided along the inside wall of the reaction vessel.

7. The reaction vessel as claimed in claim 6, wherein said stirrer comprises a rotatable shaft with liquid agitation means and wherein said porous annular pipe is provided at the end of a hollow inlet conduit for said solvent-catalyst liquid mixture to be sprayed, said inlet conduit surrounding the shaft of the stirrer.

8. The reaction vessel as claimed in claim 2, wherein said stirrer comprises a rotatable shaft with liquid agitation means and wherein said plurality of hollow pipes is provided at the end of a hollow inlet conduit surrounding the shaft of the stirrer.

9. The reaction vessel as claimed in claim 4, wherein said stirrer comprises a rotatable shaft with liquid agitation means and wherein said hollow disc is provided at the end of a hollow inlet conduit surrounding the shaft of the stirrer.

10. The reaction vessel as claimed in claim 5, wherein said stirrer comprises a rotatable shaft with liquid agitation means and wherein said spray nozzle is provided at the end of a hollow inlet conduit surrounding the shaft of the stirrer.

11. The reaction vessel of claim 1 wherein said spraying means is located at a position of about 1/15 to 1/5 times the height of the reaction vessel above the interface between the vapor-phase portion and the liquid-phase portion in the reaction vessel.

* * * * *